US008507550B2

(12) United States Patent
Swift

(10) Patent No.: US 8,507,550 B2
(45) Date of Patent: Aug. 13, 2013

(54) TREATMENT FOR ALTITUDINAL HYPOXIA

(75) Inventor: Robert Swift, Fort Collins, CO (US)

(73) Assignee: AesRx LLC, Newton, MA (US)

( * ) Notice: Subject to any disclaimer, the term of this patent is extended or adjusted under 35 U.S.C. 154(b) by 0 days.

(21) Appl. No.: 13/109,495

(22) Filed: May 17, 2011

(65) Prior Publication Data

US 2012/0041060 A1 Feb. 16, 2012

Related U.S. Application Data

(60) Provisional application No. 61/345,748, filed on May 18, 2010.

(51) Int. Cl.
*A61K 31/341* (2006.01)
*A61P 43/00* (2006.01)

(52) U.S. Cl.
USPC .......................................................... 514/461

(58) Field of Classification Search
USPC .......................................................... 514/461
See application file for complete search history.

(56) References Cited

U.S. PATENT DOCUMENTS

2002/0065232 A1 5/2002 Butler
2004/0157801 A1* 8/2004 Safo et al. ..................... 514/109

OTHER PUBLICATIONS

John B. West, Oxygen enrichment of room air to relieve the hypoxia of high altitude, Respiration Physiology, 99 (1995) 225-232.*
Jay F. Storz, Hemoglobin Function and Physiological Adaptation to Hypoxia in High-Altitude Mammals, Journal of Mammalogy, 88(1):24-31, 2007.*
Stein, JC; et al., "Capiliary oxygen transport during severe hypoxia: role of hemoglobin oxygen affinity" J. Appl. Physiol, Oct. 1993, vol. 75 No. 4; pp. 1601-1607.
Hsia. C; "Respiratory Function of Hemoglobin", New England J. of Medicine, Jan. 22, 1998, vol. 338 No. 4; pp. 239-247.
Cabrales, P; et al., "Moduiation of Perfusion and Oxygination by Red Blood Cell Oxygen Affinity during Acute Anemia", Am. J. Respir. Cell Mol. Biol. 2008, vol. 38; pp. 354-361.
Hebbel, RP; et al., "Human llamas: adaptation to altitude in subjects in subjects with high hemolobin oxygen affinity". J. Clin. Invest. Sep. 1978, vol. 62, No. 3, pp. 593-600.
Storz, JF; et al., "Hemoglobin Function and Physiological Adaptation to Hypoxia in High Altitude Mammals", J. Mammology, Feb. 1, 2007, vol. 86(1) pp. 24-31.
Cabrales, P; et al., "Regulation of perfusion and oxygen by erythrocyte hemoglobin oxygen affinity", FASEB J. 2008; 22:1141.23.
Burki, NK: et al., The Effects of Acetazolamide on the Ventilatory Response to High Altitude Hypoxia, Chest, vol. 101 No. 3, 1992, pp. 736-741.
Li, M; et al., "The protective role of 5-HMF against hypoxic injury", Cell Stress and Chaperones USA vol. 16' No. 3, May 2011, pp. 267-273.
Abdukmalik, O; et al., "5-hydroxymethyl-2-furfural modifies intracellular sickle haemoglobin and inhibits sickling of red blood cells", British J. Haematology, vol. 128, No. 4, Feb. 2005, pp. 552-561.
Dempsey, J .M.; et al., "HbO2 dissociation in man during prolonged work in chronic hypoxia" J. Appl. Physiol, Jun. 1975, vol. 38 No. 6; pp. 1022-1029.
Winslow, R.M.: at al., "Variability of oxygen affinity of blood: human subjects native to high altitude" 1981, vol. 51 pp. 11411-1416.
Mairbaurl, O.O; et al.. "Interactions between Hb, Mg, DPG, ATP,and Ci determine the change in Hb-O2 affinity at high altitude"; J. Appl. Physiol, Jul., 1993; vol. 74; pp. 40-48.
Winslow, R.M.,"The role of hemoglobin oxygen affinity in oxygen transport at high altitude" 2007, vol. 158; pp. 121-127.
Bencowitz. H.Z.; at al., "Effect of change in P50 on excercise tolerance at high altitude: a theoretical study"; J. Appl. Physic, Jul. 1982; vol. 53; pp. 1487-1495.
Mason, R.J.; et al , Excerpt from "Murray & Nadel's Textbook of Respiratory Medicine"; 5th ed. vol. II; 2010; pp. 1660-1661.
George, R. B; at al., Excerpt from "Chest Medicine, Essentials of Pulmonary Care and Critical Care Medicine"; 5th ed. vol. II; 2006; p. 45.

* cited by examiner

*Primary Examiner* — Sreeni Padmanabhan
*Assistant Examiner* — Jason A Deck
(74) *Attorney, Agent, or Firm* — Wayne A. Keown

(57) ABSTRACT

The invention provides a method for treating hypoxia caused by high altitude by administering to a subject a compound that reduces the $P_{50}$ of hemoglobin for oxygen.

15 Claims, No Drawings

TREATMENT FOR ALTITUDINAL HYPOXIA

This application claims priority to U.S. Provisional Application No. 61/345,738, filed May 18, 2010, the contents of which are hereby incorporated by reference.

BACKGROUND OF THE INVENTION

1. Field of the Invention

The invention relates to alleviation of symptoms of hypoxia resulting from reduced oxygen levels at high altitudes.

2. Summary of the Related Art

Hemoglobin is the oxygen transporter and regulator in blood. Each hemoglobin molecule can bind up to four oxygen atoms. The oxygen tension (in millimeters of mercury) at which the oxygen binding sites of hemoglobin are 50 percent saturated is called $P_{50}$. $P_{50}$ is inversely related to the binding affinity of hemoglobin for oxygen. Standard $P_{50}$ is the $P_{50}$ under standard conditions of 37° C., pH 7.4, carbon dioxide tension of 40 mm Hg at sea level, normally 26.3 mm Hg for a resting adult. However, important physiologic effects are determined by in vivo $P_{50}$, which changes rapidly in responses to body temperature, carbon dioxide tension and pH.

As body temperature increases, the affinity of hemoglobin for oxygen decreases, raising the $P_{50}$ and facilitating oxygen release. Lactic acidosis due to muscular activity further increases this effect. This is beneficial during prolonged heavy exercise. High levels of oxygen reduce $P_{50}$ and increase the affinity of hemoglobin for oxygen. In contrast, low levels of oxygen increase $P_{50}$ and decrease the affinity of hemoglobin for oxygen.

Taken together, these factors lead to a seriously decreased affinity of hemoglobin for oxygen under conditions of exercise at oxygen-depleted high altitudes. For example, at an altitude of 3,100 m a $P_{50}$ of 29 mm Hg at rest and 38 mm Hg during heavy exercise have been observed. Thus, the primary limitation on oxygen transport at high altitude is impaired loading of oxygen onto hemoglobin caused by alveolar hypoxia.

Some animals indigenous to high altitudes, such as yaks, llamas and alpacas have high affinity hemoglobins having $P_{50}$ about 10 mm Hg lower than in related lowland species due to amino acid substitutions in the globin chain. In fact, humans with the hemoglobin mutation Andrew-Minneapolis, resulting in a $P_{50}$ of 17 mm Hg, have better physiologic function at high altitudes than normal subjects whose P50 is 26.3 mm Hg. However, as a result of having evolved at lower altitudes, most humans have an inappropriate increase of $P_{50}$ at high altitudes, resulting in debilitating symptoms of hypoxia. There is no FDA approved drug that improves (lowers) the P50 and thus increases Hb affinity for oxygen in normal subjects. However, 5-HMF was evaluated for its effects on P50 in preclinical studies using sickle cell disease (SCD) red cells. These RBCs have a diminished oxygen carrying capacity due to amino acid changes in Hb structure as a result of a genetic mutation. Abdulmalik, Br. J. Haematol. 128:552-561 (2004), teaches that 5-HMF provides in vivo protection against the lethal effects of hypoxia in a sickle cell disease mouse model, and that this is the result of a lower P50 (left shift) in the SCD Hb, thus reducing the formation of sickled red blood cells in conditions of low oxygen in the inspired air. Thus, according to Abdumalik, the beneficial effect of 5-HMF in prolonging survival in the hypoxic state is due to the inhibition of RBC sickling, a phenomenon that is unique to SCD and would not be found in normal subjects. There is a need for new treatments for alleviating the symptoms of hypoxia in normal humans at high altitudes.

BRIEF SUMMARY OF THE INVENTION

The invention provides a new method for the treatment of altitudinal hypoxia. The method according to the invention comprises administering to a human subject encountering or about to encounter conditions of low oxygen a compound that decreases $P_{50}$ of hemoglobin for oxygen. The method according to the invention prevents, reduces or alleviates symptoms of hypoxia. In preferred embodiments, the compound is administered at a dosage sufficient to provide in the subject a $P_{50}$ of hemoglobin from about 15 mm Hg to about 20 mm Hg under standard conditions of 37° C., pH 7.4, carbon dioxide tension of 40 mm Hg at sea level. Preferred compounds for such method include 5-hydroxymethyl-2-furfural, 5-ethyl-2-furfural, 5-methyl-2-furfural, 2-furfural and combinations or prodrugs thereof.

DETAILED DESCRIPTION OF THE PREFERRED EMBODIMENTS

The invention provides a new method for the treatment of altitudinal hypoxia. The method according to the invention comprises administering to a human subject encountering or about to encounter conditions of low oxygen a compound that decreases $P_{50}$ of hemoglobin for oxygen, hence increasing the affinity of Hb for oxygen. The method according to the invention prevents, reduces or alleviates symptoms of hypoxia. In preferred embodiments, the compound is administered at a dosage sufficient to provide in the subject a $P_{50}$ of hemoglobin from about 15 mm Hg to about 20 mm Hg under standard conditions.

For purposes of the invention, the term "a human subject encountering or about to encounter conditions of low oxygen" means a person who is either under conditions of low oxygen or about to be under conditions of low oxygen. The term "low oxygen" is intended to mean a concentration of oxygen typically found at elevations at or above about 1,500 meters above sea level and especially at 3,000 or more meters above sea level. The term "standard conditions" means the conditions of an average adult at rest at about 37° C., pH 7.4, carbon dioxide tension of 40 mm Hg at sea level. The term "prevents or alleviates symptoms" means to stop or reduce the development of symptoms or to eliminate or reduce existing symptoms. "Symptoms" include, without limitation, reduced oxygenation of blood, red blood cells, and/or tissues, as well as impaired mental function and/or reduced ability to exercise. Such symptoms can be measured using standard techniques, such as pulse oximetry, blood gases analysis and exercise tolerance testing.

In certain preferred embodiments, the subject is either at, or about to be transported to, an elevation of from about 1,500 meters to about 9,000 meters above sea level. In certain preferred embodiments, the subject is either at, or about to be transported to, an elevation of from about 3,000 meters to about 9,000 meters above sea level.

In certain preferred embodiments, the compound is selected from the group consisting of 5-hydroxymethyl-2-furfural, 5-ethyl-2-furfural, 5-methyl-2-furfural, 2-furfural and combinations or prodrugs thereof. In certain preferred embodiments, the compound is 5-hydroxymethyl-2-furfural or a prodrug thereof. For purposes of the invention, a "prodrug of a compound" is a derivative of a compound that is metabolized in vivo to produce the compound. Typically, such prodrugs include esters and amides of the compound.

Preparation of prodrugs of preferred compounds utilizes art recognized techniques, such as those taught in U.S. Pat. No. 7,160,910.

In certain preferred embodiments, the compound is administered at a dosage sufficient to provide in the subject a $P_{50}$ of hemoglobin for oxygen of from about 17 mm Hg to about 20 mm Hg under standard conditions. The dosage required to produce such a $P_{50}$ will depend upon several factors, such as the age, weight, health and fitness of the subject, and can be determined routinely. Preferred compounds for use in the method according to the invention are non-toxic at the concentrations to produce the desired $P_{50}$. For example, 5-hydroxymethyl-2-furfural is found in foods that are consumed on a daily basis, such as coffee and caramel products, at a concentration above 6 g/kg. In rats, the acute oral $LD_{50}$ of 5-HMF is 2.5 g/kg for males and 2.5-5.0 g/kg for females (US EPA, 1992).

In some embodiments the human is administered from about 20 mg to about 10,000 mg 5-HMF. In some embodiments the human is administered from about 20 mg to about 300 mg 5-HMF. In some embodiments the human is administered from about 20 mg to about 200 mg 5-HMF. In some embodiments the human is administered from about 20 mg to about 100 mg 5-HMF. In some embodiments the human is administered from about 300 mg to about 10,000 mg 5-HMF. In some embodiments the human is administered from about 300 mg to about 5,000 mg 5-HMF. In some embodiments the human is administered from about 300 mg to about 3,000 mg 5-HMF. In some embodiments the human is administered from about 300 mg to about 1,500 mg 5-HMF. In some embodiments the human is administered from about 1,500 mg to about 10,000 mg 5-HMF. In some embodiments the human is administered from about 1,500 mg to about 5,000 mg 5-HMF. In some embodiments the human is administered from about 1,500 mg to about 3,000 mg 5-HMF. In some embodiments the human is administered from about 3,000 mg to about 10,000 mg 5-HMF. In some embodiments the human is administered from about 3,000 mg to about 5,000 mg 5-HMF.

Administration of the compounds can be by any suitable route, including, without limitation, parenteral, oral, sublingual, transdermal, topical, intranasal, inhalation, intratracheal, or intrarectal. In some preferred embodiments, administration is orally, by injection, or by inhalation.

The compounds used in the present invention may be present in any suitable diluent, carrier or excipient.

The compounds used in the method of the present invention may form salts which are also within the scope of this invention. The term "salt(s)", as employed herein, denotes acidic and/or basic salts formed with inorganic and/or organic acids and bases. Pharmaceutically acceptable (i.e., non-toxic, exhibiting minimal or no undesired toxicological effects, physiologically acceptable) salts are preferred.

As used herein, the term "pharmaceutically acceptable salts" is intended to mean salts that retain the desired biological activity of the compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The following example is intended to further illustrate an embodiment of the invention and is not intended to limit its scope.

EXAMPLE

Treatment of Hypoxia Induced by Moderate Exercise at Elevated Altitude

A 40 year old 90 kg male in good health is transported from low elevation (<100 meters above sea level) to an altitude of 3,000 meters above sea level and kept at rest there for 3 hours. At that point, the subject is tested for respiration rate, heart rate and extremity $O_2$. The subject is then put on a stationary exercise bike and allowed to ride the bike at a cadence of 40 rpm for one hour. The subject is again tested for respiration rate, heart rate and extremity $O_2$. Then the subject is transported back to low elevation. The following day, the subject is again transported to the altitude of 3,000 meters above sea level and administered a dosage of 5-hydroxymethyl-2-furfural that has previously been determined to produce in the subject a $P_{50}$ of hemoglobin for oxygen of 18 mm Hg under standard conditions. The subject is kept at rest there for 3 hours, then tested for respiration rate, heart rate and extremity $O_2$. The subject is then put on a stationary exercise bike and allowed to ride the bike at a cadence of 40 rpm for one hour. The subject is again tested for respiration rate, heart rate and extremity $O_2$. The data from the two days are then compared. It is expected that the measured parameters will be closer to normal on day 2 than on day 1.

What is claimed is:

1. A method for treating a human encountering or about to encounter conditions of low oxygen comprising administering to the subject 5-HMF in a dosage sufficient to provide in the subject a $P_{50}$ of hemoglobin from about 15 mm Hg to about 20 mm Hg under standard conditions, wherein the treatment prevents, or reduces, or alleviates symptoms of hypoxia.

2. The method according to claim 1, wherein the human is at or about to be transported to, an altitude of from about 1,500 meters to about 9,000 meters above sea level.

3. The method according to claim 2, wherein the subject is at, or about to be transported to an altitude of from about 3,000 meters to about 9,000 meters above sea level.

4. The method according to claim 1, wherein the dosage is sufficient to provide in the subject a $P_{50}$ of hemoglobin from about 17 mm Hg to about 20 mm Hg under standard conditions.

5. The method according to claim 1, wherein the human is administered from about 300 mg to about 10,000 mg 5-HMF.

6. The method according to claim 1, wherein the human is administered from about 300 mg to about 5,000 mg 5-HMF.

7. The method according to claim 1, wherein the human is administered from about 300 mg to about 3,000 mg 5-HMF.

8. The method according to claim 1, wherein the human is administered from about 300 mg to about 1,500 mg 5-HMF.

9. The method according to claim 1, wherein the human is administered from about 1,500 mg to about 10,000 mg 5-HMF.

10. The method according to claim 1, wherein the human is administered from about 1,500 mg to about 5,000 mg 5-HMF.

11. The method according to claim 1, wherein the human is administered from about 1,500 mg to about 3,000 mg 5-HMF.

12. The method according to claim 1, wherein the human is administered from about 3,000 mg to about 10,000 mg 5-HMF.

13. The method according to claim 1, wherein the human is administered from about 3,000 mg to about 5,000 mg 5-HMF.

14. The method according to claim 1 wherein the compound is administered orally, by injection, or by inhalation.

15. The method according to claim 1 wherein the compound is administered daily.

* * * * *